United States Patent
Werneth (10) Patent No.: US 6,676,690 B2
(45) Date of Patent: *Jan. 13, 2004

(54) INFLATABLE HEAT TRANSFER APPARATUS

(75) Inventor: Randell Werneth, Poway, CA (US)

(73) Assignee: Innercool Therapies, Inc., San Diego, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 09/885,655

(22) Filed: Jun. 20, 2001

(65) Prior Publication Data

US 2001/0032004 A1 Oct. 18, 2001

Related U.S. Application Data (63) Continuation of application No. 09/414,184, filed on Oct. 7, 1999, now Pat. No. 6,325,818.

(51) Int. Cl.[7] .............. A61F 7/12; A61B 18/18
(52) U.S. Cl. .............. 607/113; 607/106; 604/113; 604/96.01; 606/21
(58) Field of Search .............. 607/113, 105, 607/106; 606/21, 23; 604/96.01, 103.06, 113

(56) References Cited

U.S. PATENT DOCUMENTS

| | | |
|---|---|---|
| 1,011,606 A | 12/1911 | Fulton |
| 2,148,541 A | 2/1939 | Dierker |
| 2,308,484 A | 1/1943 | Auzin et al. |
| 2,374,609 A | 4/1945 | McCollum |
| 2,466,042 A | 4/1949 | Reich et al. |
| 2,615,686 A | 10/1952 | Davidson |
| 2,672,032 A | 3/1954 | Towse |
| 2,913,009 A | 11/1959 | Kuthe |
| 3,125,096 A | 3/1964 | Antiles et al. |
| 3,298,371 A | 1/1967 | Lee |
| 3,425,419 A | 2/1969 | Dato |
| 3,460,538 A | 8/1969 | Armstrong |
| 3,504,674 A | 4/1970 | Swenson et al. |

(List continued on next page.)

FOREIGN PATENT DOCUMENTS

| | | |
|---|---|---|
| AU | 730835 B2 | 3/2001 |
| AU | 734506 B2 | 6/2001 |

(List continued on next page.)

OTHER PUBLICATIONS

Alfonsi, P., D. I. Sessler, B. Du Manoir, J–C. Levron, J–P. Le Moing, M. Chauvin, The Effects of Meperidine and Sufentanil on the Shivering Threshold in Postoperative Patients, Anesthesiology, Jul. 1998, 89(1):43–48.

(List continued on next page.)

*Primary Examiner*—Roy D. Gibson
*Assistant Examiner*—Jocelyn Ram
(74) *Attorney, Agent, or Firm*—Gerald W. Spinks (57) ABSTRACT

An apparatus having an inflatable balloon near a distal end of a multi-lumen catheter, with a plurality of blood flow passageways formed through the interior of the balloon from a proximal face of the inflated balloon to a distal face of the inflated balloon. A heat transfer solution is introduced through a supply lumen of the catheter to inflate the balloon in a selected blood vessel; this allows blood to flow through the blood flow passageways of the balloon, from one exterior face of the balloon to another exterior face. The heat transfer solution continues to circulate around the blood flow passageways inside the balloon, to change the blood temperature, eventually exiting the balloon through a return lumen of the catheter.

14 Claims, 2 Drawing Sheets

U.S. PATENT DOCUMENTS

| | | |
|---|---|---|
| 3,604,419 A | 9/1971 | Diskin et al. |
| 3,612,175 A | 10/1971 | Ford et al. |
| 3,768,484 A | 10/1973 | Gawura |
| 3,839,621 A | 10/1974 | Hariu |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,153,048 A | 5/1979 | Magrini |
| 4,160,455 A | 7/1979 | Law |
| 4,190,033 A | 2/1980 | Foti |
| 4,216,767 A | 8/1980 | Aoshiro |
| 4,231,425 A | 11/1980 | Engstrom |
| 4,241,729 A | 12/1980 | Aoshiro |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,427,009 A | 1/1984 | Wells et al. |
| 4,445,500 A | 5/1984 | Osterholm |
| 4,464,172 A | 8/1984 | Lichtenstein |
| 4,483,341 A | 11/1984 | Witteles |
| 4,484,586 A | 11/1984 | McMickle et al. |
| 4,497,890 A | 2/1985 | Helbert |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara et al. |
| 4,655,746 A | 4/1987 | Daniels et al. |
| 4,672,962 A | 6/1987 | Hershenson |
| 4,731,072 A | 3/1988 | Aid |
| 4,739,492 A | 4/1988 | Cochran |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,799 A | 11/1988 | Herbert, Jr. et al. |
| 4,796,640 A | 1/1989 | Webler |
| 4,817,624 A | 4/1989 | Newbower |
| 4,819,655 A | 4/1989 | Webler |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowley et al. |
| 4,964,409 A | 10/1990 | Tremulis |
| 4,973,493 A | 11/1990 | Guire |
| 4,979,959 A | 12/1990 | Guire |
| 5,000,734 A * | 3/1991 | Boussignac et al. ... 604/103.06 |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishiwara et al. |
| 5,106,368 A | 4/1992 | Uldall et al. |
| 5,108,390 A | 4/1992 | Potocky et al. |
| RE33,911 E | 5/1992 | Samson et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,151,578 A | 9/1992 | Phillips |
| 5,156,151 A | 10/1992 | Imran |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,236,908 A | 8/1993 | Gruber et al. |
| 5,239,999 A | 8/1993 | Imran |
| 5,246,421 A | 9/1993 | Saab |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,279,299 A | 1/1994 | Imran |
| 5,281,213 A | 1/1994 | Milder et al. |
| 5,281,215 A | 1/1994 | Milder |
| 5,295,949 A | 3/1994 | Hathaway |
| 5,306,261 A | 4/1994 | Alliger et al. |
| 5,310,440 A | 5/1994 | Zingher |
| 5,322,514 A | 6/1994 | Steube et al. |
| 5,322,515 A | 6/1994 | Karas et al. |
| 5,322,518 A | 6/1994 | Schneider et al. |
| 5,326,165 A | 7/1994 | Walthall et al. |
| 5,326,166 A | 7/1994 | Walthall et al. |
| 5,330,435 A | 7/1994 | Vaillancourt |
| 5,330,519 A | 7/1994 | Mason et al. |
| 5,334,193 A | 8/1994 | Nardella |
| 5,342,301 A | 8/1994 | Saab |
| 5,342,621 A | 8/1994 | Eury |
| 5,344,436 A | 9/1994 | Fontenot et al. |
| 5,344,740 A | 9/1994 | Iwasawa et al. |
| 5,354,272 A | 10/1994 | Swendson et al. |
| 5,358,486 A | 10/1994 | Saab |
| 5,364,364 A | 11/1994 | Kasvikis et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,405,371 A | 4/1995 | Augustine et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Alliger et al. |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,496,311 A | 3/1996 | Abele et al. |
| 5,499,973 A | 3/1996 | Saab |
| 5,520,682 A | 5/1996 | Baust et al. |
| 5,531,776 A | 7/1996 | Ward et al. |
| 5,536,247 A | 7/1996 | Thornton |
| 5,545,133 A | 8/1996 | Burns et al. |
| 5,545,708 A | 8/1996 | Onwunaka et al. |
| 5,549,559 A | 8/1996 | Eshel |
| 5,554,119 A | 9/1996 | Harrison et al. |

| Patent | Date | Inventor |
|---|---|---|
| 5,558,644 A | 9/1996 | Boyd et al. |
| 5,569,195 A | 10/1996 | Saab |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,342 A | 4/1997 | Younger |
| 5,624,392 A | 4/1997 | Saab |
| 5,630,837 A | 5/1997 | Crowley |
| 5,642,197 A | 6/1997 | Tuhro et al. |
| 5,643,197 A | 7/1997 | Brucker et al. |
| 5,647,051 A | 7/1997 | Neer |
| 5,653,692 A | 8/1997 | Masterson et al. |
| 5,676,693 A | 10/1997 | LaFontaine |
| 5,709,654 A | 1/1998 | Klatz et al. |
| 5,713,941 A | 2/1998 | Robins et al. |
| 5,716,386 A | 2/1998 | Ward et al. |
| 5,733,318 A | 3/1998 | Augustine |
| 5,733,319 A | 3/1998 | Neilson et al. |
| 5,735,809 A | 4/1998 | Gorsuch |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,486 A | 9/1998 | Thome et al. |
| 5,800,488 A | 9/1998 | Crockett |
| 5,800,493 A | 9/1998 | Stevens et al. |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,833,673 A | 11/1998 | Ockuly et al. |
| 5,834,465 A | 11/1998 | Olney |
| 5,837,003 A | 11/1998 | Ginsburg |
| 5,861,021 A | 1/1999 | Thome et al. |
| 5,868,735 A | 2/1999 | Lafontaine |
| 5,871,468 A | 2/1999 | Kramer et al. |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,891,094 A | 4/1999 | Masterson et al. |
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,910,104 A | 6/1999 | Dobak, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,917 A | 9/1999 | Doiron et al. |
| 5,957,963 A | 9/1999 | Dobak, III |
| 5,964,751 A | 10/1999 | Amplatz et al. |
| 5,967,976 A | 10/1999 | Larsen et al. |
| 5,968,009 A | 10/1999 | Siman |
| 5,971,979 A | 10/1999 | Joye et al. |
| 5,989,238 A | 11/1999 | Ginsburg |
| 6,007,692 A | 12/1999 | Herbert et al. |
| 6,011,995 A | 1/2000 | Guglielmi et al. |
| 6,019,783 A | 2/2000 | Philips et al. |
| 6,022,336 A | 2/2000 | Zadno-Azizi et al. |
| 6,024,740 A | 2/2000 | Lesh et al. |
| 6,033,383 A * | 3/2000 | Ginsburg .................... 604/113 |
| 6,042,559 A | 3/2000 | Dobak, III |
| 6,051,019 A | 4/2000 | Dobak, III |
| 6,063,101 A | 5/2000 | Jacobsen et al. |
| 6,096,068 A | 8/2000 | Dobak, III et al. |
| 6,106,518 A | 8/2000 | Wittenberger et al. |
| 6,110,168 A | 8/2000 | Ginsburg |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,164,283 A | 12/2000 | Lesh |
| 6,165,207 A | 12/2000 | Balding et al. |
| 6,182,666 B1 | 2/2001 | Dobak, III |
| 6,190,354 B1 | 2/2001 | Sell et al. |
| 6,194,899 B1 | 2/2001 | Ishihara et al. |
| 6,206,004 B1 | 3/2001 | Schmidt et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,093 B1 | 6/2001 | Valley et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,277,143 B1 | 8/2001 | Klatz et al. |
| 6,287,326 B1 | 9/2001 | Pecor |
| 6,290,697 B1 | 9/2001 | Tu et al. |
| 6,290,717 B1 | 9/2001 | Philips |
| 6,295,990 B1 | 10/2001 | Lewis et al. |
| 6,299,599 B1 | 10/2001 | Pham et al. |
| 6,306,161 B1 | 10/2001 | Ginsburg |
| 6,312,452 B1 | 11/2001 | Dobak, III et al. |
| 6,315,754 B1 | 11/2001 | Daoud et al. |
| 6,319,248 B1 | 11/2001 | Nahon |
| 6,325,818 B1 * | 12/2001 | Werneth ................ 604/103.06 |
| 6,336,911 B1 | 1/2002 | Westerbeck |
| 6,338,727 B1 | 1/2002 | Noda et al. |
| 6,354,099 B1 | 3/2002 | Bieberich |
| 6,355,029 B1 | 3/2002 | Joye et al. |
| 6,364,899 B1 | 4/2002 | Dobak, III |
| 6,368,304 B1 | 4/2002 | Aliberto et al. |
| 6,379,378 B1 | 4/2002 | Werneth et al. |
| 6,383,210 B1 | 5/2002 | Magers et al. |
| 6,393,320 B2 | 5/2002 | Lasersohn et al. |
| 6,405,080 B1 | 6/2002 | Lasersohn et al. |
| 6,409,747 B1 | 6/2002 | Gobin et al. |
| 6,416,533 B1 | 7/2002 | Gobin et al. |
| 6,419,643 B1 | 7/2002 | Shimada et al. |
| 6,432,102 B2 | 8/2002 | Joye et al. |
| 6,432,124 B1 | 8/2002 | Worthen et al. |
| 6,436,130 B1 | 8/2002 | Philips et al. |
| 6,436,131 B1 | 8/2002 | Ginsburg |
| 6,447,474 B1 | 9/2002 | Balding |
| 6,450,990 B1 | 9/2002 | Walker et al. |
| 6,454,792 B1 | 9/2002 | Noda et al. |
| 6,454,793 B1 | 9/2002 | Evans et al. |
| 6,458,150 B1 | 10/2002 | Evans et al. |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 | 6/2001 | Ginsburg et al. |

| | | | | | | |
|---|---|---|---|---|---|---|
| 2001/0007951 A1 | 7/2001 | Dobak, III | | WO | WO 95/01814 | 1/1995 |
| 2001/0008975 A1 | 7/2001 | Dobak, III et al. | | WO | WO 96/40347 | 12/1996 |
| 2001/0010011 A1 | 7/2001 | Aliberto et al. | | WO | WO 97/01374 | 1/1997 |
| 2001/0011184 A1 | 8/2001 | Dobak, III et al. | | WO | WO 97/25011 | 7/1997 |
| 2001/0011185 A1 | 8/2001 | Dobak, III et al. | | WO | WO 97/32518 | 9/1997 |
| 2001/0014802 A1 | 8/2001 | Tu | | WO | WO 98/26831 | 6/1998 |
| 2001/0016763 A1 | 8/2001 | Lasheras et al. | | WO | WO 98/31312 | 7/1998 |
| 2001/0016764 A1 | 8/2001 | Dobak, III | | WO | WO 98/49957 | 11/1998 |
| 2001/0021865 A1 | 9/2001 | Dobak, III et al. | | WO | WO 99/02096 | 1/1999 |
| 2001/0021866 A1 | 9/2001 | Dobak, III et al. | | WO | WO 99/37226 | 7/1999 |
| 2001/0027333 A1 * | 10/2001 | Schwartz ............... 607/105 | | WO | WO 99/44519 | 9/1999 |
| 2001/0029394 A1 | 10/2001 | Dobak, III et al. | | WO | WO 99/48449 | 9/1999 |
| 2001/0031946 A1 | 10/2001 | Walker et al. | | WO | WO 99/56812 | 11/1999 |
| 2001/0032003 A1 | 10/2001 | Pecor | | WO | WO 00/38601 | 12/1999 |
| 2001/0032004 A1 | 10/2001 | Werneth | | WO | WO 99/66970 | 12/1999 |
| 2001/0039440 A1 | 11/2001 | Lasheras et al. | | WO | WO 99/66971 | 12/1999 |
| 2001/0041923 A1 | 11/2001 | Dobak, III | | WO | WO 00/09054 | 2/2000 |
| 2001/0044644 A1 | 11/2001 | Keller et al. | | WO | WO 00/47145 | 2/2000 |
| 2001/0047191 A1 | 11/2001 | Lasersohn et al. | | WO | WO 00/10494 | 3/2000 |
| 2001/0047192 A1 | 11/2001 | Lasersohn et al. | | WO | WO 00/48670 | 8/2000 |
| 2001/0047196 A1 | 11/2001 | Ginsburg et al. | | WO | WO 00/51534 | 9/2000 |
| 2001/0049545 A1 | 12/2001 | Lasersohn et al. | | WO | WO 00/53135 | 9/2000 |
| 2002/0002394 A1 | 1/2002 | Dobak, III | | WO | WO 00/57823 | 10/2000 |
| 2002/0004675 A1 | 1/2002 | Lasheras | | WO | WO 00/62837 | 10/2000 |
| 2002/0007179 A1 | 1/2002 | Dobak, III et al. | | WO | WO 00/66053 | 11/2000 |
| 2002/0007202 A1 | 1/2002 | Dobak, III et al. | | WO | WO 00/72779 | 12/2000 |
| 2002/0007203 A1 | 1/2002 | Gilmartin et al. | | WO | WO 00/72787 | 12/2000 |
| 2002/0016621 A1 | 2/2002 | Werneth et al. | | WO | WO 01/03606 | 1/2001 |
| 2002/0022823 A1 | 2/2002 | Luo et al. | | WO | WO 01/08580 | 2/2001 |
| 2002/0026227 A1 | 2/2002 | Phillips | | WO | WO 01/10323 | 2/2001 |
| 2002/0029016 A1 | 3/2002 | Pham et al. | | WO | WO 01/10365 | 2/2001 |
| 2002/0032430 A1 | 3/2002 | Luo et al. | | WO | WO 01/12061 | 2/2001 |
| 2002/0032474 A1 | 3/2002 | Dobak, III et al. | | WO | WO 01/12122 | 2/2001 |
| 2002/0040717 A1 | 4/2002 | Dobak, III | | WO | WO 01/13809 | 3/2001 |
| 2002/0045852 A1 | 4/2002 | Saab | | WO | WO 01/13837 | 3/2001 |
| 2002/0045892 A1 | 4/2002 | Kramer | | WO | WO 01/17471 | 3/2001 |
| 2002/0045925 A1 | 4/2002 | Keller et al. | | WO | WO 01/19447 | 3/2001 |
| 2002/0049409 A1 | 4/2002 | Noda et al. | | WO | WO 01/26590 | 4/2001 |
| 2002/0049410 A1 | 4/2002 | Noda et al. | | WO | WO 01/30413 | 5/2001 |
| 2002/0049484 A1 | 4/2002 | Werneth et al. | | WO | WO 01/41708 | 6/2001 |
| 2002/0056281 A1 | 5/2002 | Bieberich | | WO | WO 01/43661 | 6/2001 |
| 2002/0066458 A1 | 6/2002 | Aliberto et al. | | WO | WO 01/49236 | 7/2001 |
| 2002/0068964 A1 | 6/2002 | Dobak, III | | WO | WO 01/52781 | 7/2001 |
| 2002/0077665 A1 | 6/2002 | Kordis et al. | | WO | WO 01/56517 | 8/2001 |
| 2002/0077680 A1 | 6/2002 | Noda | | WO | WO 01/58397 | 8/2001 |
| 2002/0082671 A1 | 6/2002 | Magers et al. | | WO | WO 01/64145 | 9/2001 |
| 2002/0091378 A1 | 7/2002 | Dobak, III et al. | | WO | WO 01/64146 | 9/2001 |
| 2002/0091429 A1 | 7/2002 | Dobak, III et al. | | WO | WO 01/66052 | 9/2001 |
| 2002/0091430 A1 | 7/2002 | Dobak, III et al. | | WO | WO 01/74276 | 10/2001 |
| 2002/0095200 A1 | 7/2002 | Dobak, III et al. | | WO | WO 01/76655 | 10/2001 |
| 2002/0095201 A1 | 7/2002 | Worthen et al. | | WO | WO 01/78580 | 10/2001 |
| 2002/0099427 A1 | 7/2002 | Dobak, III | | WO | WO 01/87379 | 11/2001 |
| 2002/0103519 A1 | 8/2002 | Dobak, III et al. | | WO | WO 01/95840 | 12/2001 |
| 2002/0111584 A1 | 8/2002 | Walker et al. | | WO | WO 02/07793 | 1/2002 |
| 2002/0120314 A1 | 8/2002 | Evans et al. | | WO | WO 02/26175 | 4/2002 |
| 2002/0128698 A1 | 9/2002 | Dobak, III et al. | | WO | WO 02/26176 | 4/2002 |
| 2002/0138122 A1 | 9/2002 | Worthen et al. | | WO | WO 02/26285 | 4/2002 |
| | | | | WO | WO 02/26307 | 4/2002 |
| | FOREIGN PATENT DOCUMENTS | | | WO | WO 02/28300 | 4/2002 |
| | | | | WO | WO 02/36180 | 5/2002 |
| AU | | 739996 B2 | 2/2002 | WO | WO 02/38091 | 5/2002 |
| AU | | 743945 B2 | 2/2002 | WO | WO 02/43577 | 6/2002 |
| EP | | 0655225 A1 | 5/1993 | WO | WO 02/47577 | 6/2002 |
| EP | | 0 664 990 | 11/1997 | WO | WO 02/47742 | 6/2002 |
| EP | | 0428505 B2 | 3/2001 | WO | WO 02/055129 | 7/2002 |
| EP | | 1172932 A2 | 7/2001 | | | |
| EP | | 1205167 A2 | 5/2002 | | | |
| EP | | 1029520 B1 | 8/2002 | | | |
| FR | | 2 447 406 | 3/1980 | | | |
| RU | | 806 029 | 2/1981 | | | |
| WO | | WO 91/05528 | 5/1991 | | | |
| WO | | WO 93/04727 | 3/1993 | | | |

OTHER PUBLICATIONS

Anon, "Automatic feedback instrumentation for hospital room utilizing microsensors," *IBM Technical Disclosure Bulletin* (*abs.*), 29(3): 1 page, Aug. 1996.

Benzinger, T.H.; On Physical Heart Regulation and Sense of Temperature in Man; Naval Medical Research Institute; Physiology; vol. 45; pp. 645–659; (Feb. 26, 1959).

Brengelmann, George L.; Specialized Brain Cooling in Humans?; The FASEB Journal; vol. 7, pp. 1148–1153 (Sep. 1993).

Buggy, D., P. Higgins, C. Moran, F. O'Donovan, and M. McCarroll, Clonidine at Induction Reduces Shivering after General Anaesthesia, 1997, pp. 263–267, Can. J. Anaesth., vol. 44, N. 3.

Cabanac, M., Selective Brain Cooling and Thermoregulatory Set–Point, 1998, pp. 3–13, Journ. of Basic & Clinical Physiology & Pharmacology, vol. 9, N. 1.

Cabanac, M.; Selective Brain Cooling in Humans: fancy or fact?; The FASEB Journal; vol. 7; pp. 1143–1147 (Sep. 1993).

Capogna, G. and D. Celleno, I. V. Clonidine for Post–Extradural Shivering in Parturients: A Preliminary Study, 1993, Brit. Journ. of Anaesth., vol. 71.

Carrol et al. "A comparison of measurements from a temporal artery thermometer and a pulmonary artery thermistor—preliminary results," Fax correspondence dated Oct. 19, 2001.

Cheng, C., T. Matsukawa, D. I. Sessler, M. Ozaki, A. Kurz, B. Merrifield, L. Hank, and P. Olofsson, Increasing Mean Skin Temperature Linearly Reduces the Core–Temperature Thresholds for Vasoconstriction and Shivering in Humans, May 1995, pp. 1160–1168, Anesthesiology, vol. 82, No. 5.

Colvett, K. T., A. F. Althausen, B. Bassil, N. M. Heney, F. V. McGovern, H. H. Young, II, D. S. Kaufman, A. L. Zietman, and W. U. Shipley, Opportunities with Combined Modality Therapy for Selective Organ Preservation in Muscle–Invasive Bladder Cancer, 1996, pp. 201–208, Journ. of Surgical Oncology, vol. 63.

DeFord et al. "Design and evaluation of closed–loop feedback control of minimun temperatures in human intracranial tumours with interstitial hyperthermia," *Med. & Biol. Eng. & Comput. 29*: 197–206, Mar. 1991.

Deklunder, G., M. Dauzat, J–L. Lecroart, J–J. Hauser, and Y. Houdas, "Influence of Ventilation of the Face on Thermoregulation in Man during Hyper– and Hypothermia," *Eur. J. Appl. Physiol.,* 1991, 62:342–348.

Gentilello, L. M., "Advances in the Management of Hypothermia," *Horizons in Trauma Surgery,* 75(2):243–256, Apr. 1995.

Giesbrecht, G. G., M. S.. L. Goheen, C. E. Johnston, G. P. Kenny, G. K. Bristow, and J. S. Hayward, Inhibition of Shivering Increases Core Temperature Afterdrop and Attenuates Rewarming in Hypothermic Humans, 1997, 0161–7567:1630–1634, The American Physiological Society.

Giuffre, M., J. Finnie, D. A. Lynam, and D. Smith, Rewarming Postoperative Patients: Lights, Blankets, or Forced Warm Air,, Dec. 1991, pp. 387–393, Journ. of Post Anaesthesia Nursing, vol. 6, N. 6.

Guffin, A., D. Girard, andJ. A. Kaplan, Shivering Following Cardiac Surgery: Hemodynamic Changes and Reversal, Feb. 1987, pp. 24–28, Journ. of Cardiothoracic Anesthesia, vol. 1, N. 1.

Haley, E. C. et al. "A Randomized Trial of Tirilazad Mesylate in Patients with Acute Stroke (RANTTAS)," *Stroke,* 27(9):1453–1458, 1996.

Iaizzo, Facial Warming Increases the Threshold for Shivering, 1999; pp. 231–239, Journ. of Neurosurgical Anesthesiology, vol. 11, No. 4.

Keegan, M. T. et al. Shivering Complicating the Treatment of Neurologically Impaired Surgical and Intensive Care Unit Patients, Anesthesiology, 91(3):874–876, Sep. 1999,.

Kogaku "Sensor technology to control artificial organs," *KLA,* 22(4):295–300, Aug. 1984 (in Japanese).

Kurz, Martin, et al.; "Naxolone, Meperidine, and Shivering."; *Anesthesiology;* 79(6):1193–1201; Dec. 1993.

Lennon, R. L., M. P. Hosking, M. A. Conover, and W. J. Perkins, Evaluation of a Forced–Air System for Warming Hypothermic Postoperative Patients, 1990, pp. 424–427, Anesth. Analg., vol. 70.

Leslie, D., D. I. Sessler, A. R. Bjorksten, M. Ozaki, T. Matsukawa, and M. Schroeder, Propofol Causes a Dose–Dependent Decrease in the Thermoregulatory Threshold for vasoconstriction but has Little Effect on Sweating, Aug. 1994, pp. 353–360, vol. 81, N. 2.

Maas, C. Intermittent Antegrade Selective Cerebral Perfusion during Circulatory Arrest for Repair of Aortic Arch. Perfusion, vol. 12, No. 2, pp. 127–132, 1997.

Matsukawa, T., A. Kurz, D. I. Sessler, A. R. Bjorksten, B. Merrifield, and C. Cheng, Propofol Linearly Reduces the Vasoconstriction and Shivering Thresholds, May 1995, pp. 1169–1180, Anesthesiology, vol. 82, N. 5.

Meden, P., K. Overgaard, H. Pedersen, G. Boysen, Effect of Hypothermia and Delayed Thrombolysis in a Rat Embolic Stroke Model, 1994, pp. 91–98, Acta Neurol. Scand. vol. 90.

Möller et al. "Temperature control and light penetration in a feedback interstitial laser thermotherapy system," *Int. J. Hyperthermia,* 12(1):49–63, 1996.

Olshausen et al. "An isothermal flowmeter with improved frequency response for measuring tissue blood flow," *Pflügers Arch.* 367:97–102, 1976.

Pais, S. O., K. D. Tobin, C. B. Austin, and L. Queral, Percutaneous Insertion of the Greenfield Inferior Vena Cava Filter: Experience with Ninety–Six Patients, Oct. 1998, pp. 460–464, Journ. of Vascular Surg., vol. 8, N. 4.

Patton, J. H, T. C. Fabian, M. A. Croce, G. Minard, F. E. Pritchard, and K. A. Kudsk, Prophylactic Greenfield Filters: Acute Complications and Long–Term Follow–Up, Aug. 1996; pp. 231–237; Journ. of Trauma: Injury, Infection, and Critical Care, vol. 41, N.2.

Rohrer, M. J. and A. M. Natale, Effect of Hypothermia on the Coagulation Cascade, Oct. 1992, pp. 1402–1405, Critical Care Medicine, vol. 20, N. 10.

Schmid–Elsaesser, R. et al. (1999), Combination Drug Therapy and Mild Hypothermia: A Promising Treatment Strategy for Reversible, Focal Cerebral Ischemia, Stroke, 1891–1899, Jun.

Sessler, Daniel I.; "Mild Perioperative Hypothermia"; The New England Journal of Medicine; 336:1730–1737; Jun. 12, 1997.

Sharkey, A., J. M. Lipton, M. T. Murphy, and A. H. Giesecke, Inhibition of Postanesthestic Shivering with Radiant Heat, Feb. 1987, pp. 249–252, Anesthesiology, vol. 66, N. 2.

Shiraki, K., N. Konda, and S. Sagawa, Esphageal and Tympanic Temperature Responses to Core Blood Temperature Change during Hyperthermia, *J. Appl. Physiol. 61(1)*:98–102 (1986).

Simon, M., C. A. Athanasoulis, D. Kim, F. L. Steinberg, D. H Porter, B. H. Byse, S. Kleshinski, S. Geller, D. E. Orron, and A. C. Waltman; Simon Nitinol Inferior Vena Cava Filter: Initial Clinical Experience, Jul. 1989, pp. 99–103; Radiology.

Villamaria, F. J., C. E. Baisden, A. Hillis, M. H. Rajab, and P. A. Rinaldi, "Forced–Air Warming is No More Effective than Conventional Methods for Raising Postoperative Core Temperature After Cardiac Surgery," *Journ. Cardiothoracic and Vascular Anesth.*, 11(6):708–711, Oct. 1997.

Zweifler, R. M. and D. I. Sessler, "Thermoregulatory Vasoconstriction and Shivering Impede Therapeutic Hypothermia in Acute Ischemic Stroke Patients," *Journ. Stroke and Cerebrovascular Diseases,* 6(2):100–104, 1996.

Ambrus; The Biphasic Nature and Temperature Dependence of the Activation of Human Plasminogen by Urokinase; May 1979; pp. 339–347; Research Communications in Chemical Pathology and Pharmacology, vol. 24, No 2.

Bigelo; Hypothermia, Its Possible Role in Cardiac Surgery; Nov. 1959; pp. 849–866; Annals of Surgery, vol. 132, No. 5.

Cheatle; Cryostripping the Long and Short Saphenous Veins; Jan. 1993; one page; Br. J. Surg., vol. 80.

Dexter; Blood Warms as It Blows Retrograde from a Femoral Cannulation Site to the Carotid Artery During Cardiopulmonary Bypass; Nov. 1994; pp. 393–397; Perfusion, vol. 9, No. 6.

Gillinov; Superior Cerebral Protection with Profound Hypothermia During Circulatory Arrest; Nov. 1992; pp. 1432–1439; Ann. Thorac. Surg., vol. 55.

Higazi; The Effect of Ultrasonic Irradiation and Temperature on Fibrinolytic Activity in Vitro; Aug. 1992; p. 251–253; Thrombosis Research, vol. 69, No. 2.

Imamaki; Retrograde Cerebral Perfusion with Hypothermic Blood Provides Efficient Protection of the Brain; Jul. 1995; pp. 325–333; Journal of Cardiac Surgery, vol. 10, No. 4, Part 1.

Jolin; Management of a Giant Intracranial Aneurysm Using Surface–Heparinized Extracorporeal Circulation and Controlled Deep Hypothermic Low Flow Perfusion; Aug. 1992; pp. 756–760; Acta Anaesthesiologica Scandinavia.

Jos. R. C. Jansen, Ph.D., et al. (1997) Near Continuous Cardiac Output b Thermodilution. Journal of Clinical Monitoring 13:233–239.

Kimoto; Open Heart Surgery under Direct Vision with the Aid of Brain–Cooling by Irrigation; Jul. 1955; pp. 592–603; Surgery, vol. 39, No. 4.

Marekovic, Z.; Abstract of Renal Hypothermia in Situ by Venous Passages: Experimental Work on Dogs; 1980; Eur Urol 6(2); 1 page.

Meden; Effect of Hypothermia and Delayed Thrombolysis in a Rat Embolic Stroke Model; Dec. 1993; pp. 91–98; Acta Neurologica Scandinavica.

Meden; The Influence of Body Temperature on Infarct Volume and Thrombolytic Therapy in a Rat Embolic Stroke Model; Feb. 1994; pp. 131–138; Brain Research, vol. 647.

Milleret, Rene; La cryo–chirurgie danes les varices des mimbres inferieurs; Angiologie; Supplement au No. 110.

Milleret; Abstract of Cryosclerosis of the Saphenous Veins in Varicose Reflux in the Obese and Elderly; 10.1981; one page; Phlebologie, vol. 34, No. 4.

Parkins; Brain Cooling in the Prevention of Brain Damage During Periods of Circulatory Occlusion in Dogs; Apr. 1954; pp. 284–289; Annals of Surgery, vol. 140, No. 3.

Piepgras; Rapid Active Internal Core Cooling for Induction of Moderate Hypothermia in Head Injury by Use of an Extracorporeal Heat Exchanger; Feb. 1998; pp. 311–318; Neurosurgery, vol. 42, No. 2.

Rijken; Plasminogen Activation of Low Temperatures in Plasma Samples Containing Therapeutic Concentrations of Tissue–Type Plasminogen Activator or Other Thrombolytic Agents; Oct. 1989; pp. 47–52; place of publication unknown.

Schwartz, A.E. et al.; (1996); Isolated cerebral hypothermia by single carotid artery perfusion of extracorporeally cooled blood in baboons; Neurosurgery 39(3):577–582.

Schwartz; Cerebral Blood Flow during Low–flow Hypothermic Cardiopulmonary Bypass in Baboons; Jun. 1994; pp. 959–964; Anesthesiology, vol. 81, No. 4.

Schwartz; Selective Cerebral Hypothermia by Means of Transfemoral Internal Carotid Artery Catheterization; May 1996; pp. 575–572; Radiology, vol. 201, No. 2.

Steen; The Detrimental Effects of Prolonged Hypothermia and Rewarming in the Dog; Aug. 1979; pp. 224–230; Anesthesiology, vol. 52, No. 3.

Vandam; Hypothermia; Sep. 1959; pp. 546–553; The New England Journal of Medicine.

White; Cerebral Hypothermia and Circulatory Arrest; Jul. 1978; pp. 450–458; Mayo Clinic Proceedings, vol. 53.

Yenari, Thrombolysis with Tissue Plasminogen Activator (TPA) is Temperature Dependent; Jul. 1994; pp. 475–481; Thrombosis Research, vol. 77, No. 5.

Yoshihara; Changes in Coagulation and Fibrinolysis Occurring in Dogs during Hypothermia; Aug. 1984; pp. 503–512; Thrombosis Research, vol. 37, No. 4.

Zarins; Circulation in Profound Hypothermia; Nov. 1972; pp. 97–104; Journal of Surgical Research, vol. 14, N. 2.

\* cited by examiner

INFLATABLE HEAT TRANSFER APPARATUS

CROSS REFERENCE TO RELATED APPLICATIONS

This application is a continuation of U.S. Application Ser. No. 09/414,184 is now U.S. Pat. No. 6,325,818 issued Dec. 4, 2001, for "Inflatable Cooling Apparatus for Selective Organ Hypothermia", filed Oct. 7, 1999.

STATEMENT REGARDING FEDERALLY SPONSORED RESEARCH OR DEVELOPMENT

Not Applicable

BACKGROUND OF THE INVENTION

1. Field of the Invention

The current invention relates to selective cooling, or hypothermia, of an organ, such as the brain, by cooling the blood flowing into the organ. This cooling can protect the tissue from injury caused by anoxia or trauma.

2. Background Information

Organs of the human body, such as the brain, kidney, and heart, are maintained at a constant temperature of approximately 37° C. Cooling of organs below 35° C is known to provide cellular protection from anoxic damage caused by a disruption of blood supply, or by trauma. Cooling can also reduce swelling associated with these injuries.

Hypothermia is currently utilized in medicine and is sometimes performed to protect the brain from injury. Cooling of the brain is generally accomplished through whole body cooling to create a condition of total body hypothermia in the range of 20° to 30° C. This cooling is accomplished by immersing the patient in ice, by using cooling blankets, or by cooling the blood flowing externally through a cardiopulmonary bypass machine.

Total body hypothermia to provide organ protection has a number of drawbacks. First, it creates cardiovascular problems, such as cardiac arrhythmias, reduced cardiac output, and increased systemic vascular resistance. These side effects can result in organ damage. These side effects are believed to be caused reflexively in response to the reduction in core body temperature. Second, total body hypothermia is difficult to administer. Immersing a patient in ice water clearly has its associated problems. Placement on cardiopulmonary bypass requires surgical intervention and specialists to operate the machine, and it is associated with a number of complications including bleeding and volume overload. Third, the time required to reduce the body temperature and the organ temperature is prolonged. Minimizing the time between injury and the onset of cooling has been shown to produce better clinical outcomes.

Some physicians have immersed the patient's head in ice to provide brain cooling. There are also cooling helmets, or head gear, to perform the same. This approach suffers from the problems of slow cool down and poor temperature control due to the temperature gradient that must be established externally to internally. It has also been shown that complications associated with total body cooling, such as arrhythmia and decreased cardiac output, can also be caused by cooling of the face and head only.

Selective organ hypothermia has been studied by Schwartz, et. al. Utilizing baboons, blood was circulated and cooled externally from the body via the femoral artery and returned to the body through the carotid artery. This study showed that the brain could be selectively cooled to temperatures of 20° C. without reducing the temperature of the entire body. Subsequently, cardiovascular complications associated with total body hypothermia did not occur. However, external circulation of the blood for cooling is not a practical approach for the treatment of humans. The risks of infection, bleeding, and fluid imbalance are great. Also, at least two arterial vessels must be punctured and cannulated. Further, percutaneous cannulation of the carotid artery is very difficult and potentially fatal, due to the associated arterial wall trauma. Also, this method could not be used to cool organs such as the kidneys, where the renal arteries cannot be directly cannulated percutaneously.

Selective organ hypothermia has also been attempted by perfusing the organ with a cold solution, such as saline or perflourocarbons. This is commonly done to protect the heart during heart surgery and is referred to as cardioplegia. This procedure has a number of drawbacks, including limited time of administration due to excessive volume accumulation, cost and inconvenience of maintaining the perfusate, and lack of effectiveness due to temperature dilution from the blood. Temperature dilution by the blood is a particular problem in high blood flow organs such as the brain. For cardioplegia, the blood flow to the heart is minimized, and therefore this effect is minimized.

Intravascular, selective organ hypothermia, created by cooling the blood flowing into the organ, is the ideal method. First, because only the target organ is cooled, complications associated with total body hypothermia are avoided. Second, because the blood is cooled intravascularly, or in situ, problems associated with external circulation of blood are eliminated. Third, only a single puncture and arterial vessel cannulation is required, and it can be performed at an easily accessible artery such as the femoral, subclavian, or brachial. Fourth, cold perfusate solutions are not required, thus eliminating problems with excessive fluid accumulation. This also eliminates the time, cost, and handling issues associated with providing and maintaining cold perfusate solution. Fifth, rapid cooling can be achieved. Sixth, precise temperature control is possible.

The important factor related to catheter development for selective organ hypothermia is the small size of the typical feeding artery, and the need to prevent a significant reduction in blood flow when the catheter is placed in the artery. A significant reduction in blood flow would result in ischemic organ damage. While the diameter of the major vessels of the body, such as the vena cava and aorta, are as large as 15 to 20 mm., the diameter of the feeding artery of an organ is typically only 4.0 to 8.0 mm. Thus, a catheter residing in one of these arteries cannot be much larger than 2.0 to 3.0 mm. in outside diameter. The small size of the feeding artery also limits the size and type of heat transfer element that can safely be used.

A catheter based on the circulation of water or saline operates on the principle of transferring heat from the blood to raise the temperature of the water. Therefore, it is essential to use a heat transfer element that transfers heat from the blood to the cooling fluid as efficiently as possible, while restricting the flow of blood as little as possible. So, it would be beneficial to have a heat transfer apparatus that can be inserted percutaneously into an artery of restricted size, that can efficiently transfer heat, and that will not significantly limit the flow rate of blood in the artery during application of cooling.

BRIEF SUMMARY OF THE INVENTION

The present invention is a cooling apparatus comprising a flexible catheter which can be inserted through the vascular system of a patient to a feeding artery, with an inflatable balloon heat exchanger near the distal end of the catheter. The present invention also encompasses a method for using such a device to perform selective organ cooling. After placement in the selected feeding artery, the heat exchanger balloon is inflated by pressurization with a saline solution, via a supply lumen in the catheter. The heat exchanger balloon has one or more blood passageways passing through it, from a proximal aspect of the balloon to a distal aspect of the balloon. When the heat exchanger balloon is inflated to contact the wall of the artery in which it is placed, each of the blood passageways comprises a tube having an inlet in one face of the heat exchanger balloon and an outlet in another face of the heat exchanger balloon, thereby allowing blood to continue flowing through the artery after inflation of the balloon. The blood passageway tubes can be constructed of a material having a relatively high thermal conductivity, such as a thin metallized polymer, such as a film with one or more metallized surfaces. Alternatively, the blood passageway tubes can be constructed of a metal-loaded polymer film. Further, the entire heat exchanger balloon can be constructed of such a material, in order to maximize the cooling capacity of the heat exchanger.

After inflation of the heat exchanger balloon, the saline solution, which is chilled by an external chiller, continues circulating through the interior of the heat exchanger balloon, around the blood passageway tubes, and back out of the balloon through a return lumen in the catheter. This cools the blood passageway tubes, which in turn cool the blood flowing through them. This cooled blood then flows through the selected organ and cools the organ.

The device can also incorporate a lumen for a guidewire, facilitating the navigation of the catheter through the vascular system of the patient.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
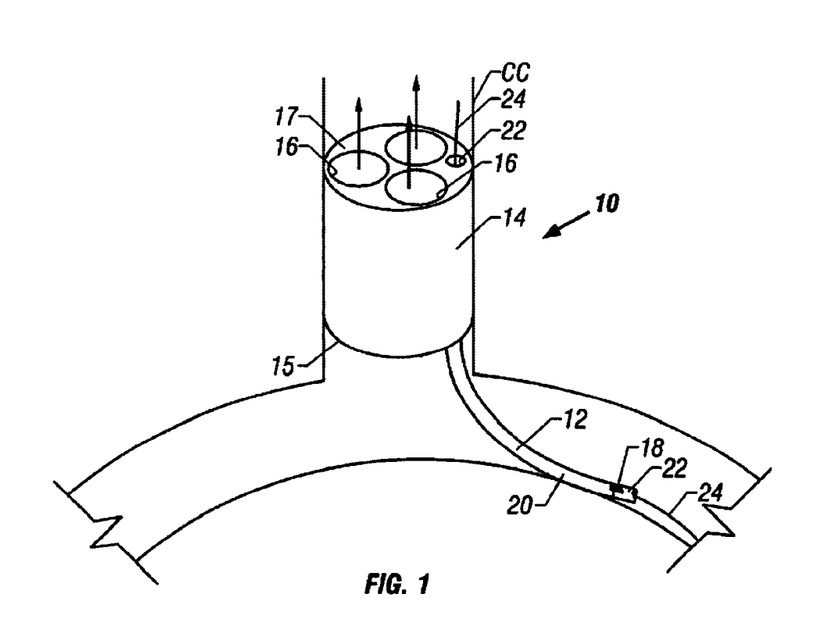
FIG. 1 is a perspective view of the device of the present invention in place in a common carotid artery of a patient.

As shown in FIG. 1, the cooling apparatus 10 of the present invention includes a flexible multilumen catheter 12, an inflatable balloon 14, and a plurality of blood flow passageways 16 through the balloon 14. The balloon 14 is shown in an inflated state, in a selected position in a common carotid artery CC.

The balloon 14 is attached near a distal end of the flexible catheter 12. The catheter 12 can have at least a cooling fluid supply lumen 18 and a cooling fluid return lumen 20, with the cooling fluid supply lumen 18 preferably being located substantially within the cooling fluid return lumen 20. The catheter 12 can also have a guidewire lumen 22, for the passage of a guidewire 24, as is known in the art.

The balloon 14 can be formed from a flexible material, such as a polymer. The balloon 14 can be constructed to assume a substantially cylindrical shape when inflated, with a proximal aspect 15 and a distal aspect 17. The balloon 14 can have a plurality of tubular shaped blood flow passageways 16 formed therethrough, from the proximal aspect 15 to the distal aspect 17. The tubular walls of the passageways 16 constitute a heat transfer surface, for transferring heat from the blood to the cooling fluid. The flexible material of the tubular passageways 16 can be, at least in part, a metallized material, such as a film coated with a thin metal layer, either internally, externally, or both, to aid in heat transfer through the passageway walls. Alternatively, the tubular passageways 16 can be constructed of a metal-loaded polymer film. Further, the remainder of the balloon 14 can be coated with a thin metallized layer, either internally, externally, or both, or a metal-loaded polymer film. The proximal aspect 15 and the distal aspect 17 of the balloon can also constitute a heat transfer surface, for transferring heat from the blood to the cooling fluid. The guidewire lumen 22 of the catheter 12 can also pass through the balloon 14, from the proximal aspect 15 to the distal aspect 17.

Figure 2:
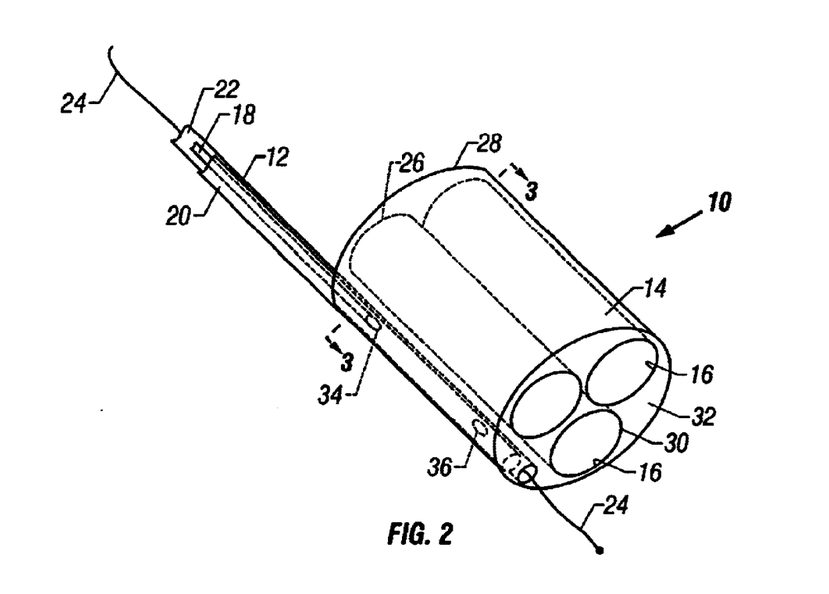
FIG. 2 is a perspective view of the device shown in FIG. 1, with additional details of construction.

As shown in FIG. 2, each tubular passageway 16 has a proximal port 26 in a proximal face 28 on the proximal aspect 15 of the balloon 14, and a distal port 30 in a distal face 32 on the distal aspect 17 of the balloon 14. A cooling fluid supply port 34 near the distal end of the cooling fluid supply lumen 18 supplies chilled saline solution from a chiller (not shown) to the interior of the balloon 14, surrounding the blood flow passageways 16. A cooling fluid return port 36 in the cooling fluid return lumen 20 returns the saline solution from the interior of the balloon 14 to the chiller. Relative placement of the cooling fluid ports 34, 36 can be chosen to establish flow counter to the direction of blood flow, if desired.

Figure 3:
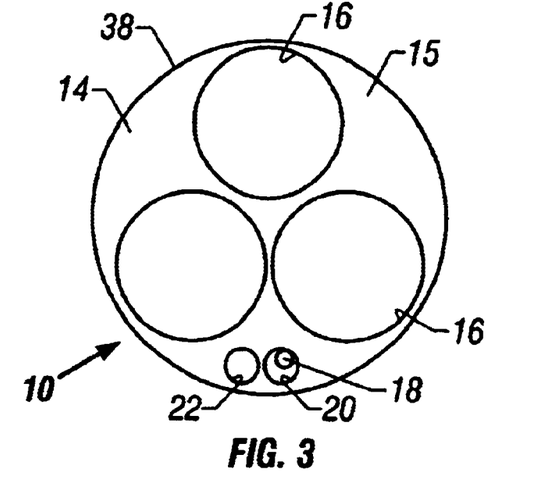
FIG. 3 is a transverse section view of the device shown in FIG. 2, along the section line 3—3.
Figure 4:
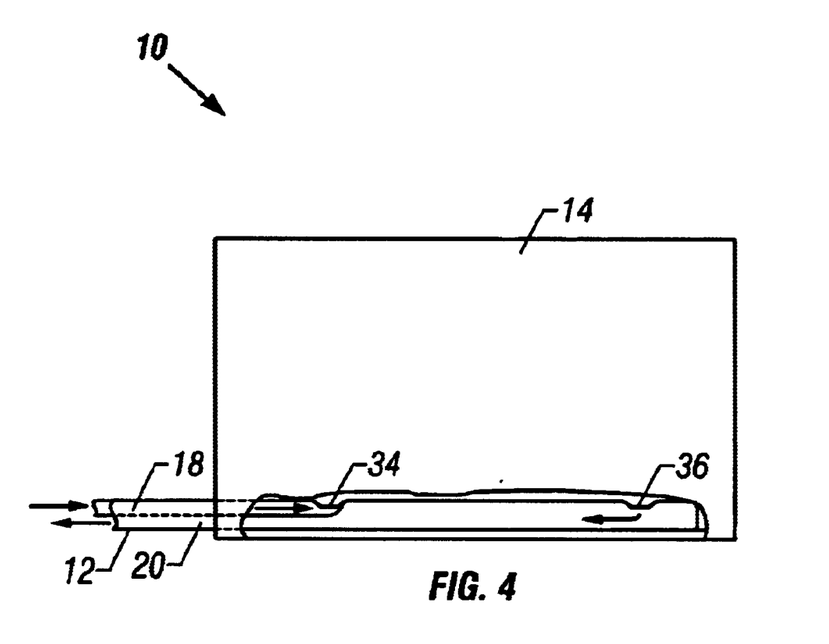
FIG. 4 is a partial longitudinal section view of the device shown in FIG. 2, showing the flow path of the cooling fluid.

FIG. 3 shows the proximal aspect 15 of the balloon 14 and gives a view through the blood flow passageways 16, illustrating the general arrangement of the blood flow passageways 16, cooling fluid supply lumen 18, cooling fluid return lumen 20, and guidewire lumen 22, within the outer wall 38 of the balloon 14. FIG. 4 is a side elevation view of the apparatus 10, with a partial longitudinal section through the balloon wall 38, showing one possible arrangement of the cooling fluid supply port 34 and the cooling fluid return port 36 within the balloon 14.

In practice, the balloon 14, in a deflated state, is passed through the vascular system of a patient on the distal end of the catheter 12, over the guidewire 24. Placement of the guidewire 24 and the balloon 14 can be monitored fluoroscopically, as is known in the art, by use of radiopaque markers (not shown) on the guidewire 24 and the balloon 14. When the balloon 14 has been positioned at a desired location in the feeding artery of a selected organ, such as in the common carotid artery feeding the brain, fluid such as saline solution is supplied through the cooling fluid supply lumen 18. This fluid passes through the cooling fluid supply port 34 into the interior of the balloon 14, surrounding the tubular passageways 16, to inflate the balloon 14. Although the balloon 14 can be formed to assume a substantially cylindrical shape upon unconstrained inflation, the balloon 14 will essentially conform to the shape of the artery within which it is inflated. As the balloon 14 inflates, the blood flow passageways 16 open, substantially assuming the tubular shape shown. When the balloon 14 has been properly inflated, blood continues to flow through the feeding artery CC by flowing through the blood flow passageways 16, as indicated, for example, by the arrows in FIG. 1. The size and number of the blood flow passageways 16 are designed to provide a desired amount of heat transfer surface, while maintaining a suitable amount of blood flow through the feeding artery CC. Return flow to the chiller can be established, to allow flow of cooling fluid through the cooling fluid return port 36 and the cooling fluid return lumen 20 to the chiller. This establishes a continuous flow of cooling fluid through the interior of the balloon 14, around the blood flow passageways 16. The return flow is regulated to maintain the balloon 14 in its inflated state, while circulation of cooling fluid takes place. The saline solution is cooled in the chiller to maintain a desired cooling fluid temperature in the interior of the balloon 14, to impart a desired temperature drop to the blood flowing through the tubular passageways 16. This cooled blood flows through the feeding artery to impart the desired amount of cooling to the selected organ. Then, cooling fluid can be evacuated or released from the balloon 14, through the catheter 12, to deflate the balloon 14, and the apparatus 10 can be withdrawn from the vascular system of the patient.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. An apparatus for changing the temperature of a patient, comprising:
   a flexible catheter;
   an inflatable balloon attached near a distal end of said catheter;
   at least one blood flow passageway formed through the interior of said balloon, said at least one blood flow passageway extending from a proximal blood flow port in a proximal exterior face of said balloon to a distal blood flow port in a distal exterior face of said balloon;
   a fluid supply lumen formed in said catheter;
   a fluid supply port in said catheter, connecting said fluid supply lumen to the interior of said balloon;
   a fluid return lumen formed in said catheter; and
   a fluid return port in said catheter, connecting the interior of said balloon to said fluid return lumen.

2. An apparatus as recited in claim 1, wherein said balloon is inflatable to a substantially cylindrical shape.

3. An apparatus as recited in claim 1, wherein said at least one blood flow passageway assumes a substantially tubular shape upon inflation of said balloon.

4. An apparatus as recited in claim 1, further comprising a guidewire lumen formed in said catheter.

5. An apparatus as recited in claim 1, further comprising a plurality of blood flow passageways formed through the interior of said balloon, each said blood flow passageway extending from a proximal blood flow port in a proximal exterior face of said balloon to a distal blood flow port in a distal exterior face of said balloon.

6. An apparatus as recited in claim 1, wherein said at least one blood flow passageway is formed from a material having high thermal conductivity.

7. An apparatus for changing the temperature of a patient, comprising:
   a flexible catheter;
   an inflatable balloon attached near a distal end of said catheter;
   at least one blood flow passageway formed through the interior of said balloon, said at least one blood flow passageway extending from a proximal blood flow port in a proximal exterior face of said balloon to a distal blood flow port in a distal exterior face of said balloon;
   a fluid supply lumen formed in said catheter;
   a fluid supply port in said catheter, connecting said fluid supply lumen to the interior of said balloon;
   a fluid return lumen formed in said catheter; and
   a fluid return port in said catheter, connecting the interior of said balloon to said fluid return lumen;
   wherein said at least one blood flow passageway is formed from a metallized polymer film.

8. An apparatus as recited in claim 7, wherein said at least one blood flow passageway is formed from a polymer film having metal layers formed on both interior and exterior surfaces.

9. An apparatus as recited in claim 7, wherein said at least one blood flow passageway is formed from a polymer film loaded with metal particles.

10. An apparatus for changing the temperature of a patient, comprising:
    a flexible catheter;
    an inflatable balloon attached near a distal end of said catheter, said balloon being inflatable to a substantially cylindrical shape;
    a plurality of blood flow passageways formed through the interior of said balloon, each said blood flow passageway extending from a proximal blood flow port in a proximal exterior face of said balloon to a distal blood flow port in a distal exterior face of said balloon, each said blood flow passageway being shaped to assume a substantially tubular shape upon inflation of said balloon, each said blood flow passageway being formed of a material having high thermal conductivity;
    a fluid supply lumen formed in said catheter;
    a fluid supply port in said catheter, connecting said fluid supply lumen to the interior of said balloon;
    a fluid return lumen formed in said catheter; and
    a fluid return port in said catheter, connecting the interior of said balloon to said fluid return lumen.

11. An apparatus as recited in claim 10, wherein each said blood flow passageway is formed from a metallized polymer film.

12. An apparatus as recited in claim 11, wherein each said blood flow passageway is formed from a polymer film having metal layers formed on both interior and exterior surfaces.

13. An apparatus as recited in claim 10, further comprising a guidewire lumen formed in said catheter.

14. A method of changing the temperature of a patient, comprising:
    providing an apparatus having a flexible multi-lumen catheter, an inflatable balloon attached near a distal end of said catheter, and at least one blood flow passageway formed through the interior of said balloon from a proximal blood flow port in a proximal exterior face of said balloon to a distal blood flow port in a distal exterior face of said balloon;
    introducing said apparatus through the vascular system of a patient to a selected location in a blood vessel;

introducing a heat transfer fluid through a first lumen of said catheter to the interior of said balloon, thereby inflating said balloon to contact the walls of said selected blood vessel, and thereby allowing blood flow through the interior of said balloon via said at least one blood flow passageway;

circulating said heat transfer fluid through the interior of said balloon, around said at least one blood flow passageway, and out of said balloon through a second lumen of said catheter, thereby changing the temperature of the wall of said at least one blood flow passageway, while maintaining said balloon in said inflated state; and changing the temperature of said blood flowing through said selected blood vessel by contact with the wall of said at least one blood flow passageway.

* * * * *